United States Patent [19]

Frassica

[11] Patent Number: 5,318,532

[45] Date of Patent: Jun. 7, 1994

[54] MULTILUMEN CATHETER WITH VARIABLE CROSS-SECTION LUMENS

[75] Inventor: James J. Frassica, Chelmsford, Mass.

[73] Assignee: C. R. Bard, Inc., Murray Hill, N.J.

[21] Appl. No.: 985,368

[22] Filed: Dec. 3, 1992

Related U.S. Application Data

[63] Continuation of Ser. No. 722,392, Jun. 19, 1991, abandoned, which is a continuation of Ser. No. 416,362, Oct. 3, 1989, abandoned.

[51] Int. Cl.[5] .............................................. A61M 29/00
[52] U.S. Cl. ........................................ 604/96; 604/53; 604/165; 606/194
[58] Field of Search ........................... 604/96–103, 604/264, 280–284, 158–163, 43–45, 53, 164, 165, 169, 246; 606/192–194

[56] References Cited

U.S. PATENT DOCUMENTS

| | | | |
|---|---|---|---|
| 1,596,754 | 10/1923 | Moschelle | 604/282 |
| 1,696,018 | 12/1928 | Schellberg | 604/39 |
| 2,548,602 | 4/1951 | Greenburg | 604/96 |
| 2,819,718 | 1/1958 | Goldman | 604/282 |
| 3,589,356 | 6/1971 | Silverman | 604/27 |
| 4,141,364 | 2/1979 | Schultze | 604/96 |
| 4,406,656 | 9/1983 | Hattler et al. | 604/280 |
| 4,479,497 | 10/1984 | Fogarty et al. | 606/194 |
| 4,589,868 | 5/1986 | Dietler | 604/96 |
| 4,606,347 | 5/1986 | Fogarty et al. | 606/194 |
| 4,710,181 | 12/1987 | Fuqua | 604/96 |
| 4,820,349 | 4/1989 | Saab | 604/194 |
| 4,861,337 | 8/1989 | George | 604/96 |
| 4,913,701 | 4/1990 | Tower | 604/103 |
| 4,932,959 | 6/1990 | Horzewski et al. | 604/96 |
| 4,941,877 | 7/1990 | Montano, Jr. | 604/96 |
| 5,035,705 | 7/1991 | Burns | 606/194 |

Primary Examiner—C. Fred Rosenbaum
Assistant Examiner—Mark Bockelman
Attorney, Agent, or Firm—Wolf, Greenfield & Sacks

[57] ABSTRACT

A catheter, such as a balloon dilatation catheter includes an outer tabular shaft having a passageway extending therethrough. A flexible inner tube extending through the passageway is attached at its ends to the shaft to form an annular inflation lumen between the shaft and inner tube and a guidewire lumen extending through the inner tube. A dilatation balloon is mounted on the shaft and is in fluid communication with the inflation lumen. Upon aspiration of the inflation lumen and dilatation balloon via an inlet port, the inner tube expands against the outer shaft providing the guidewire lumen with a relatively large cross-sectional area for free movement of the guidewire. Upon injection of an inflation liquid into the inflation lumen, the inner tube collapses about the in-dwelling guidewire creating an inflation lumen having a large cross-sectional area enabling rapid inflation and deflation of the dilatation balloon. In another embodiment another flexible inner tube is provided to define a third intermediate annular lumen which may be pressurized to securely couple the catheter to the guidewire to increase the column strength of the assembly and enhance the pushability of the catheter through a stenosis.

22 Claims, 2 Drawing Sheets

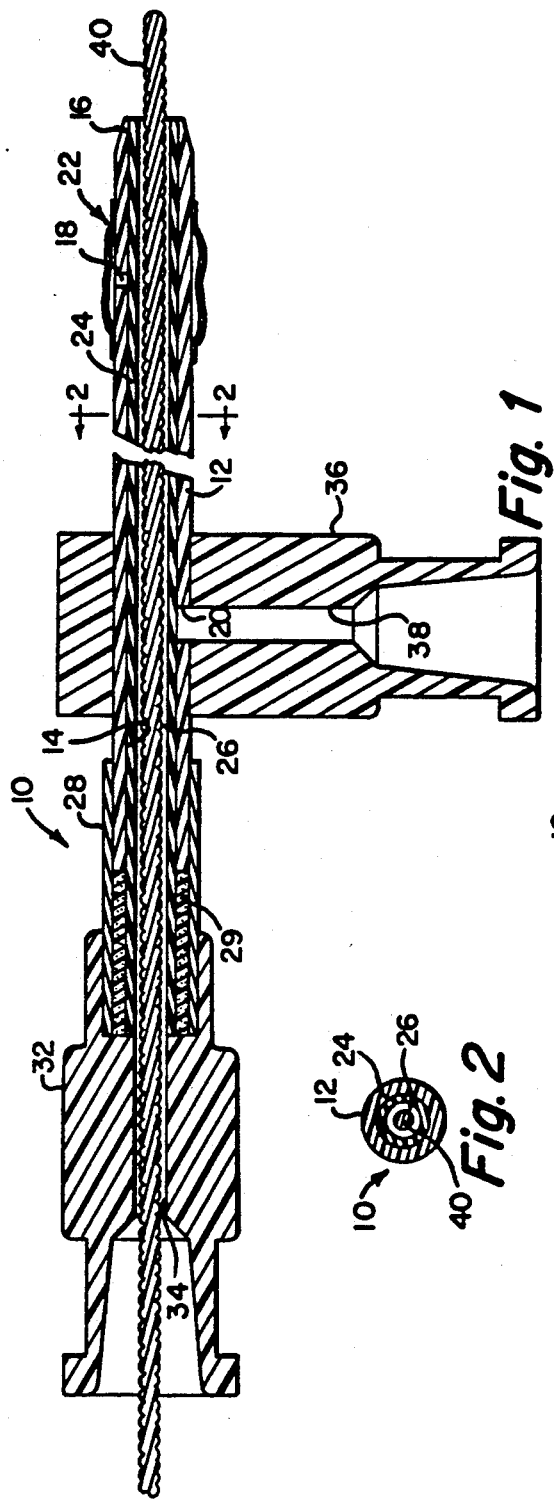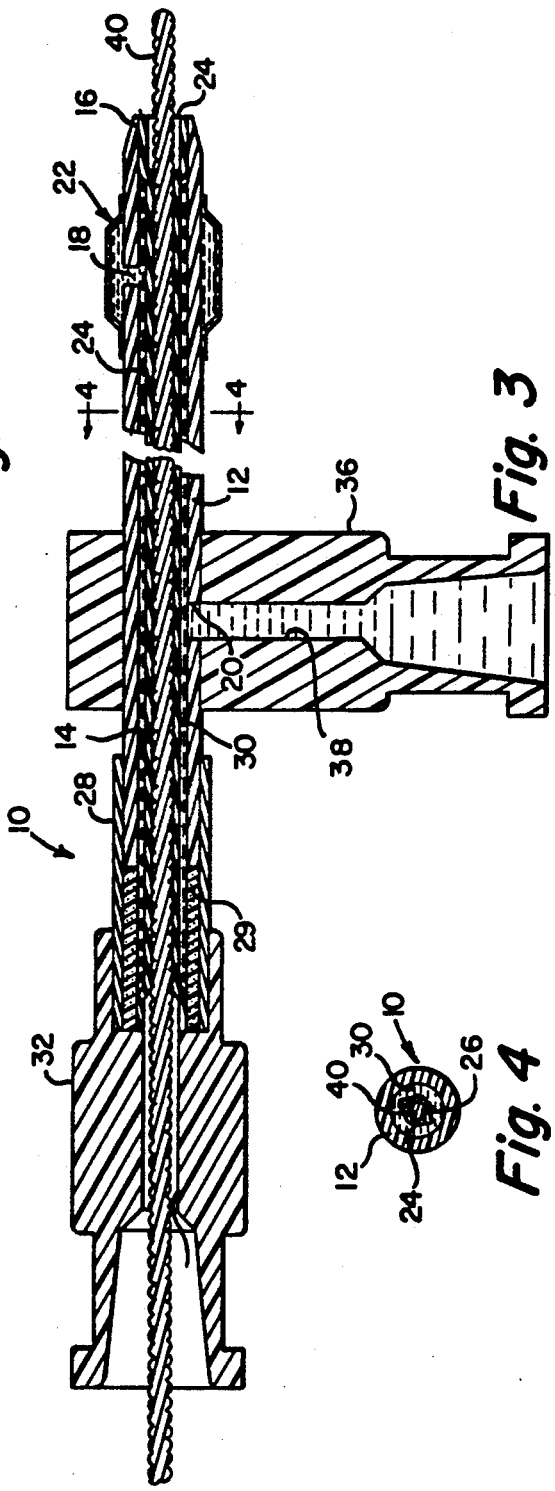

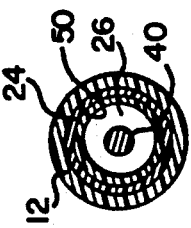
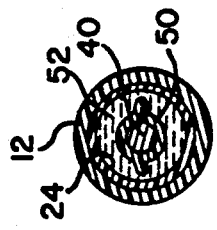
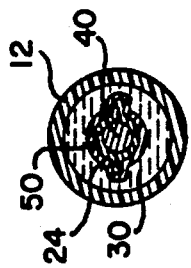
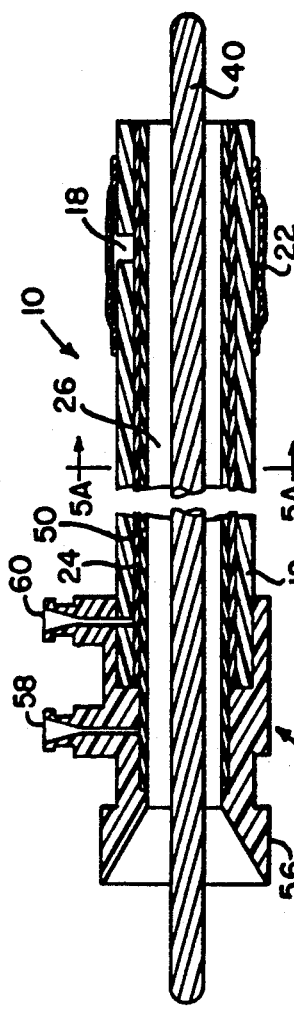
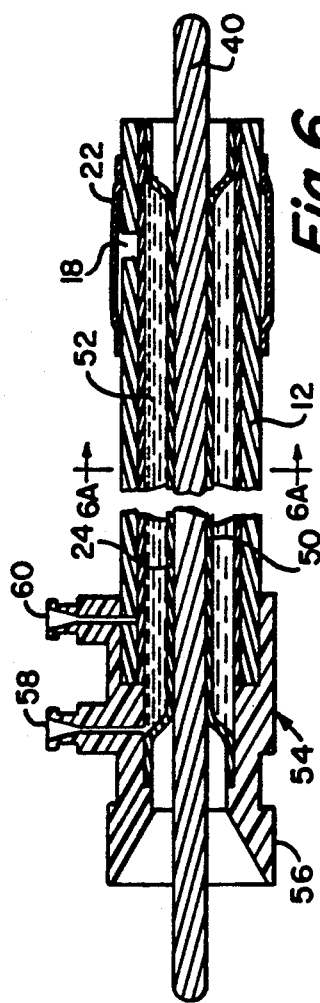
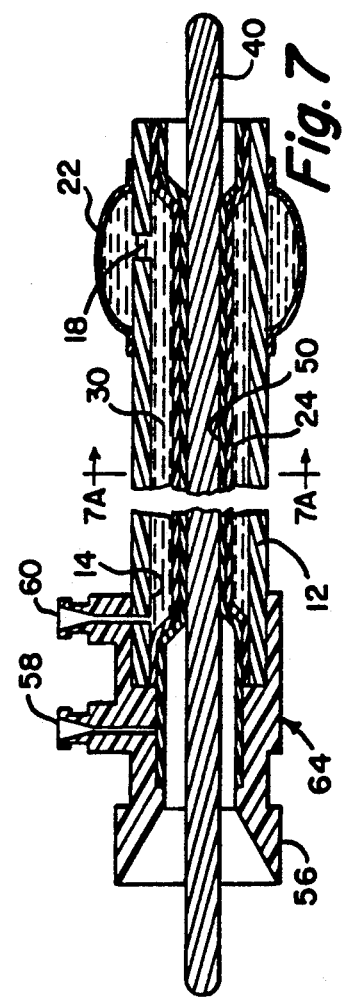

MULTILUMEN CATHETER WITH VARIABLE CROSS-SECTION LUMENS

This application is a continuation of application Ser. No. 07/722,392, filed Jun. 19, 1991, now abandoned, which is a continuation of application Ser. No. 07/416,362, filed Oct. 3, 1989, now abandoned.

FIELD OF THE INVENTION

The invention relates to catheters, and particularly to catheters having multiple lumens for multiple functions, such as, for example balloon angioplasty catheters.

BACKGROUND OF THE INVENTION

Catheters are commonly used to perform a wide variety of medical procedures within human body lumens. Often, depending on the type of procedure involved, a catheter may desirably be used to perform multiple functions. It is common for such catheters to have multiple lumens, each dedicated to the performance of a particular function. For example, in many types of balloon catheters, it is common for the catheter to have two lumens, one for inflation or deflation of the balloon, and another to provide direct communication from the proximal to the distal end of the catheter, such as to deliver medication, contrast liquid or the like or to withdraw blood or other fluid from the body lumen. By way of further example, one such balloon catheter commonly in use is that employed in percutaneous transluminal angioplasty (PTA) procedures, in which a balloon dilatation catheter is inserted into a patient's artery for the purpose of enlarging a blood vessel which has become obstructed as a result of arteriosclerosis. Such angioplasty catheters typically are guided through the patient's arterial system to the site of the obstruction (the stenosis) by a guidewire over which the catheter is passed. After the guidewire has been passed through the stenosis, the catheter then is advanced over the guidewire to place the balloon (while in a deflated condition) within the stenosis. Once so placed, the balloon is inflated with an inflation liquid under a high-pressure, sometimes as much as the order of about 20 atmospheres, to forcibly dilate the stenosis and enlarge the lumen in the artery, thereby improving blood flow through the artery. such catheters require two lumens, one for inflation or deflation of the balloon and the other for reception of the guidewire. Typically, the guidewire lumen also may be used to deliver liquids out of the distal end of the catheter or to take blood pressure measurements.

It is a desirable objective of such catheters to maximize the cross-sectional flow area of each of the lumens. For example, it is advantageous to provide a relatively large cross-sectional flow area for the inflation/deflation lumen in order that the time required to inflate and deflate the balloon is kept at a minimum. It also is desirable to maintain a relatively large cross-sectional area for the guidewire lumen to facilitate freedom of movement of the guidewire within the lumen as well as to provide a relatively large fluid flow area for infusion of liquids and for measurement of blood pressure. A significant competing consideration, however, is the importance of maintaining the outer diameter of the catheter as small as possible. Maintaining a small outer diameter for the catheter is important in order to permit the catheter to be advanced into relatively small diameter arteries as well as to facilitate advancement of the deflated balloon of the catheter into the stenosis to be treated. If the diameter of the catheter is too large, it may not be able to reach into a small artery or, even if it can be inserted into the artery, it may not be able to cross the stenosis. As a result, the catheters of the prior art typically have reduced the size of one lumen in order to increase the size of another.

There is a need, therefore, for a catheter configuration in which the cross-sectional area of each of the lumens may be maximized without increasing the outer diameter of the catheter. It is among the general objects of the invention to provide a catheter construction that satisfies that need.

SUMMARY OF THE INVENTION

A multilumen catheter, in accordance with the present invention, has an elongate flexible hollow tubular shaft having a main passageway extending therethrough. At least one flexible member divides the passageway into a plurality of lumens. The flexible member is constructed and arranged so as to enable collapse of lumens which are not being utilized at the time while maximizing the cross-sectional area of the lumen in use.

In one embodiment of the present invention, a balloon dilatation catheter includes an elongate flexible outer tubular shaft having a balloon at its distal end, a main passageway extending therethrough and a distal inflation port extending through the shaft wall. A flexible inner tube extends through the passageway of the outer tube and is attached at its ends to the interior of the outer tube, thereby defining an annular inflation lumen between the inner and outer tubes. The inflation lumen communicates with the interior of the balloon through the distal port in the wall of the outer tube. A proximal inflation port is attached to the proximal end of the catheter and communicates with the inflation lumen. The lumen in the inner tube serves as a guidewire lumen.

In accordance with the illustrative embodiment of the invention the pressures within the lumens are controlled thereby enabling enlargement of the cross-sectional area of one of the lumens while reducing the cross-sectional area of the other. The cross-sectional area of the lumens thus may be controlled to provide the desired maximum cross-sectional area in the lumen that is in use. Thus, when a negative pressure is introduced into the inflation lumen, the inner tube expands against the outer tube, providing the guidewire lumen with a large cross-sectional area in which a guidewire is free to move or which is better adapted to transport liquids or fluid pressures. Alternately, when an inflation liquid is introduced under positive pressure into the inflation lumen, the inner tube is forced radially inwardly, away from the outer tube and into contracting configuration about the in-dwelling guidewire, providing the inflation lumen with a large cross-sectional area for passage of the inflation liquid.

In another embodiment of the invention, adapted particularly for use in balloon angioplasty catheters, a third lumen is defined by providing an additional inner tube within the above-mentioned inner tube, so that the first mentioned inner tube serves as an intermediate tube. The inner and intermediate flexible tubes thus define an additional annular lumen therebetween and an inflation/deflation port is provided to apply positive, negative or atmospheric pressure to the intermediate lumen. When providing positive pressure to the intermediate lumen the inner tube is caused to constrict tightly about and grip the guidewire disposed within the guidewire lumen. In that configuration, the overall column strength and "pushability" of the catheter-guidewire combination is increased. Such increased pushability is important particularly when it becomes necessary to advance the distal end of the balloon dilatation catheter into a tight stenosis.

It is among the objects of the present invention to provide a catheter having a reduced overall cross-sectional area.

Another object of the invention is to provide a multilumen catheter in which the cross-sectional area defined by one lumen may be increased while the cross-sectional area defined by the other lumen(s) is decreased.

A further object of the invention is to provide a multilumen catheter in which the cross-sectional areas of the lumens may be varied without varying the overall outer diameter of the catheter.

Another object of the present invention is to provide a balloon dilatation catheter with a variable cross section inflation lumen which, during use, defines a maximum cross-sectional area for faster inflation and deflation.

A further object of the present invention is to provide a dilatation catheter with a variable cross-section guidewire lumen which, during use, has a large cross-sectional area to permit free movement of the guidewire as well as distal dye injections and pressure measurement.

Another object of the invention is to provide a balloon dilatation catheter for use with a movable guidewire in which the catheter may be secured, releasably and temporarily, to the guidewire to enhance the column strength and pushability of the catheter.

Yet another object of the present invention is to provide a multilumen catheter in which a maximum amount of the overall cross-sectional area of the catheter is utilized by the involved lumen during each catheter function.

DESCRIPTION OF THE DRAWINGS

The foregoing and other advantages of the invention will be appreciated more fully from the following further description thereof, with reference to the accompanying drawings wherein:

FIG. 1 is a longitudinal sectional, fragmented diagrammatic illustration of one embodiment of the catheter of the present invention in which the inflation lumen is collapsed and the guidewire lumen is open;

FIG. 2 is a sectional illustration through the catheter as seen along line 2—2 of FIG. 1;

FIG. 3 is a longitudinal sectional, fragmented illustration of the catheter of FIG. 1 in which the inflation lumen is open and the guidewire lumen is collapsed;

FIG. 4 is a sectional illustration through the catheter as seen along line 4—4 of FIG. 3;

FIG. 5 is a diagrammatic illustration of another embodiment of the invention by which the catheter may be releasably and temporarily connected to the guidewire to enhance the column strength and pushability of the catheter and in which the catheter has an intermediate lumen between the inflation and guidewire lumen, with the guidewire lumen being shown in its maximum cross-sectional configuration;

FIG. 5A is a cross-sectional illustration seen along the line 5A—5A of FIG. 5;

FIG. 6 is a diagrammatic illustration of the embodiment of FIG. 5 in which the intermediate lumen is inflated to temporarily attach the catheter to the guidewire; and FIG. 6A is a cross-sectional illustration seen along the line 6A—6A of FIG. 6;

FIG. 7 is a diagrammatic illustration of the embodiment of FIG. 5 in which the balloon is inflated, and FIG. 7A is a cross-sectional illustration seen along the line 7A—7A of FIG. 7.

DESCRIPTION OF THE ILLUSTRATIVE EMBODIMENT

As shown in FIG. 1 a balloon dilatation catheter 10 includes an elongate, flexible, tubular shaft 12 formed from an appropriate polymeric material. The catheter has a proximal end, seen to the left in FIG. 1, and a distal end, seen to the right in FIG. 1. The shaft 12 may be extruded from polyethylene and may have an external diameter of 0.039 inches and internal diameter of 0.032 inches. The shaft 12 may be approximately 135 cm in length. A passage or lumen 14 extends longitudinally through shaft 12 from the proximal end to the distal end. An internal annular recess 16 is provided at the distal end of passage 14, enlarging the diameter of the passage slightly.

As shown in FIGS. 1-3, a distal inflation port 18 is formed through the wall of the shaft 12 in the distal region for providing fluid communication with the interior of the dilatation balloon, indicated generally at 22. The port 18 may be circular in shape with a diameter of approximately 0.020 inches. A proximal inflation port 20 extends through the wall of the shaft 12 in the proximal region of the shaft 12 for providing fluid communication between lumen 14 and a luer fitting 36. The proximal inflation port 20 also may be circular in shape with a diameter of approximately 0.020 inches.

In the illustrative embodiment of the invention, the lumen 14 contains a flexible, elongate thin-walled, inner tube, the lumen 26 defined by the inner tube 24 serving as a guidewire lumen. The inner tube 24 may be substantially coextensive in length with the shaft 12. The inner tube 24 is attached to the distal end of the shaft 12 at internal recess 16 by an appropriate adhesive compatible with the tube materials. The proximal ends of shaft 12 and inner tube 24 are coaxially disposed within a tubular segment 28 that provides proximal strength and is adhesively secured therein. The proximal ends of the shaft 12, inner tube 24 and tubular segment 28 are secured together at adhesive bond 29.

The inner tube 24 is unattached to the shaft 12 between its proximal and distal adhesive bonds thereby defining a variably shaped, generally annular inflation lumen 30 between the inner tube 24 and the interior surface of the shaft 12. The inner tube 24 may be formed from a highly flexible polymeric material such as polyethylene terephthalate (PET). Due to the highly flexible nature of inner tube 24, the guidewire and inflation lumens 26, 30 have cross-sectional areas which vary inversely, depending on the pressure applied to the inflation lumen 30 via inlet port 20. The inner tube 24 may have an external diameter of 0.029 to 0.031 inches, and a wall thickness of the order of 0.001", or less.

The tubular segment 28 provides increased column strength for the proximal end of shaft 12 and flexible liner 24. Tubular segment 28 may be made from a metal such as stainless steel hypodermic tubing and, for example, may have an internal diameter of 0.039 inches and an external diameter of 0.050 inches. The proximal end of tubular segment 28 is connected to a luer fitting 32 which provides fluid communication between guidewire lumen 26 and a device (not shown), for introducing a contrast liquid into the patient's artery or for performing arterial pressure measurements.

A dilatation balloon 22 is attached to the exterior of shaft 12 in the distal region, as shown in FIG. 1. The balloon 22 may be formed from a polymeric material, such as polyethylene terephthalate, bonded at its proximal and distal ends to shaft 12 with an appropriate adhesive. The balloon may be made in the manner described in U.S. Pat. No. 4,490,421 (Levy). The inflated diameter of dilatation balloon 22 may be between about 2.0 to 5.0 mm and its length may be of the order of about 20 mm. The interior of balloon 22 is in fluid communication with inflation lumen 30 through outlet port 18.

A balloon inflation luer fitting 36 is mounted to the shaft 12 and is coupled to proximal inflation port 20 to provide a means for introducing an inflation medium for positively or negatively pressurizing inflation lumen 30 with an inflation/deflation device, such as a syringe (not shown).

From the foregoing it will be appreciated that, the cross-sectional areas of inflation lumen 30 and guidewire lumen 26 vary inversely with respect to each other. In a first mode of operation, as when it is desired to permit relative movement of the guidewire through the guidewire lumen 26 or to facilitate liquid infusion into or pressure measurement within the patient's artery, a negative pressure is applied to the inflation lumen 30 at proximal port 20 and the fitting 36. As suggested in FIG. 1, application of negative pressure to the inflation lumen aspirates the interior of the balloon 22 and inflation lumen 30 causing the flexible inner tube 24 to expand radially outwardly against the inner lumen of the shaft 12, as shown in FIGS. 1 and 2. In this mode, inflation lumen 30 is at a minimum cross-sectional configuration while guidewire lumen 26 is at a maximum cross-sectional configuration. The increased cross-sectional area of guidewire lumen 26 permits free movement of guidewire 40, as well as dye injections and distal pressure monitoring.

In a second mode of operation, as shown in FIGS. 3 and 4, an inflation liquid is applied under positive pressure to inflation lumen 30 via proximal port 20. The pressure of the inflation liquid forces the flexible inner tube 24 away from the interior wall of shaft 12 into a contracted configuration about the guidewire 40. In this mode, the guidewire lumen 26 is at a reduced cross-sectional area while inflation lumen 30 is at an increased cross-sectional area. The increased cross-sectional area of inflation lumen 30 permits flow of inflation liquid at a greater flow rate, resulting in rapid inflation and deflation of balloon 22.

By way of further example of the manner in which the balloon dilatation catheter as described above may be of use in angioplasty of a stenosis in a patient's artery, the catheter typically will be pre-assembled with a guidewire 40. The guidewire 40 may be of the small diameter steerable type, such as described in U.S. Pat. No. 4,545,390 (Leary). The guidewire and catheter are assembled in the configuration illustrated in FIG. 1 in which the inflation lumen is either aspirated or is at atmospheric pressure. The assembled catheter and guidewire then are advanced through a previously placed guide catheter which serves to guide the assembled dilatation catheter and guidewire toward the site of the stenosis. When the dilatation catheter has projected slightly beyond the distal end of the guide catheter, further advancement of the dilatation catheter typically will be halted to permit the guidewire to be advanced and manipulated independently so as to pass the guidewire through the stenosis to be dilated. Typically, the guidewire will be manipulated from its proximal end to cause the guidewire to extend out of the dilatation catheter and along the patient's arteries towards the stenosis. As described more fully in the aforementioned Leary patent the guidewire is manipulable as to be steerable through the patient's arteries. The distal end of the guidewire is radiopaque so that its progress may be monitored under fluoroscopy.

In accordance with the present invention, during advancement and manipulation of a guidewire it is desirable that the guidewire lumen present minimal resistance to movement of the guidewire. Accordingly, when in that mode, the inflation lumen 26 is aspirated to enlarge the flexible inner tube 24 to its maximum diameter. At this time, there is no need for the balloon to be inflated and, therefore, it is appropriate to maintain the balloon and the inflation lumen in an aspirated configuration. During advancement of the guidewire through the patient's arteries, the physician typically will cause a radiopaque liquid to be injected into the patient's artery, either through the guide catheter or through the guidewire lumen of the dilatation catheter (or both) in order that the shape and configuration of the artery may be observed fluoroscopically. During this phase of the procedure, therefore, it is desirable that the guidewire lumen be maintained in as open a configuration as possible, possibly to permit dye injection through the guidewire lumen even while the guidewire is in place.

Once the guidewire 40 has been suitably placed through the stenosis, the dilatation catheter 10 is advanced over the guidewire and is guided to and through the stenosis, with the balloon 22 being located within the stenosis. During this manipulation it is desired to maintain the balloon catheter in a deflated configuration and in a low profile to facilitate passage of the balloon portion of the catheter into the stenosis. It is also important during this phase that there be minimal resistance to advancement of the catheter over the guidewire and, accordingly, both of these objectives are achieved by retaining the inflation lumen and the balloon in a deflated condition during this phase.

Once the balloon catheter has been advanced so that the balloon is within the stenosis the balloon is inflated under high pressure, sometimes as high as approximately 20 atmospheres, to dilate the stenosis and enlarge the lumen of the artery thereby to reestablish improved blood flow through the artery. In order to inflate the balloon the inflation liquid is applied under pressure through the fitting 36 and the inflation lumen 30. Inflation under pressure causes the flexible inner tube 24 to collapse radially inwardly about the guidewire 40 as suggested in FIGS. 3 and 4. Collapse of the inner tube 24 increases the annular cross-sectional area of the inflation lumen 30 to the maximum extent permitted by the presence of the guidewire 40. The maximum cross-sectional flow area though the inflation lumen enables the balloon to be inflated and deflated rapidly. It is desirable for the physician to be able to inflate and deflate the balloon as quickly as possible. After the dilatation procedure has been completed, the balloon 22 and inflation lumen 30 are aspirated to cause the balloon to collapse and permit removal of the catheter from the patient's artery.

FIGS. 5–7 illustrate, diagrammatically, another embodiment of the invention which incorporates a plurality of flexible internal divider elements so as to define three lumens within the catheter. This embodiment of the invention, in addition to providing the functions described above in connection with the first embodiment (FIGS. 1–4), provides a further mode of operation by which the catheter may be securely anchored to the guidewire while maintaining the balloon in a deflated configuration. In this additional mode of operation, the guidewire enhances the column strength of the catheter so that together they have an increased pushability and are better able to be pushed through a stenosis. This is particularly desirable when encountering a tight stenosis which otherwise may be difficult or perhaps impossible to cross with the catheter.

The above-described modified embodiment is illustrated in FIGS. 5–7, in which corresponding components have the same reference numerals as the first described embodiment. Thus, this embodiment of the invention has a flexible tubular catheter shaft 12 having a proximal (to the left) and a distal end (to the right). A balloon 22 is mounted on the distal end of the shaft. In this embodiment of the invention, the catheter includes two flexible tubes within the lumen 14 of the catheter shaft, including an inner flexible tube 50 and an intermediate tube 24 which corresponds to the identically numbered tube described above in connection with the embodiments of FIGS. 1–4. Both of the tubes 24, 50 may be formed from a thin flexible material such as polyethylene terephthalate and may be of the order of 0.001" or less wall thickness. The inner tube 50 has an expanded outer diameter substantially equal to the expanded inner diameter of the intermediate tube 24. The expanded outer diameter of the intermediate tube 24 is substantially equal, or very slightly less than the inner diameter of the flexible tubular shaft 12. The arrangement of the tubular catheter shaft 12, intermediate flexible tube 24 and inner flexible tube 50 define an arrangement of three lumens including an inner guidewire lumen 26, and outer inflation/deflation annular lumen 30 and an intermediate annular lumen 52, between the inner and outer lumens. The catheter 10' is provided, at its proximal end, with a fitting 54 which may be molded from an appropriate plastic material. The fitting 54 is attached, as by adhesive, to the proximal end of the catheter shaft 12. The inner flexible tube 50 and intermediate tube 24 are attached, as by adhesive, at their proximal ends, to the proximal end of the fitting 54 and, in the case of the intermediate flexible tube 24, also to the proximal end of the catheter end of the shaft 12. The distal end of the flexible tubes 24, 50 are attached to each other and to the distal end of the catheter shaft 12.

The fitting 54 includes an axial luer portion 56 that communicates directly with the inner guidewire lumen 26. The fitting 54 also includes a luer fitting 58 that communicates with the intermediate lumen 52. The fitting 54 also includes a third luer fitting 60 (which corresponds to fitting 36 in FIG. 1) which communicates with the inflation/deflation lumen 30.

The embodiment of the invention illustrated in FIGS. 5–7 has three modes of operation. In a first mode of operation, illustrated in FIGS. 5 and 5A the outer and intermediate lumens 30, 52 are maintained in aspirated configuration, which also maintains the balloon in a deflated low profile. In this configuration the inner lumen 26 is in its maximum cross-sectional configuration in which the catheter and guidewire are free to move relative to each other. In this configuration the catheter may be tracked over the guidewire so as to follow the guidewire toward the stenosis to be treated. Additionally, the enlarged cross-sectional area of the guidewire lumen 26 also enhances the ability of the lumen to infuse liquids and to transmit fluid pressure to enhance blood pressure measurements. In this configuration both inflation ports 58 and 60 are connected to inflation/deflation devices (such as syringes) which are operated to maintain a negative pressure on the intermediate and outer lumens.

In accordance with the modified embodiment of the invention, when the catheter has been tracked along the guidewire to a location where the distal end of the catheter is disposed in readiness as to be pushed through the stenosis, the catheter can be configured to be securely coupled to the guidewire so that the guidewire and catheter may be pushed together through the stenosis. By coupling the guidewire to the catheter during this phase of the procedure the column stiffness of the catheter is increased to enhance the pushability of the catheter through the stenosis. As described above, this is particularly important when a stenosis is unusually tight and difficult to cross with the catheter. In order to configure the catheter for this mode of operation, the inflation/deflation port 60 is maintained under a negative pressure while the port 58 which is in communication with the intermediate annular lumen 52 is exposed to liquid under a high pressure. In this configuration, illustrated in FIG. 6 and 6A, the balloon is maintained in its low profile configuration while the inner flexible tube 50 is contracted radially inwardly into firm engagement about the guidewire 40. The catheter is thus coupled to the guidewire by the inner tubular element 50. The catheter and guidewire thus may be advanced together through the stenosis.

The third mode of operation of the modified catheter is illustrated in FIGS. 7 and 7A in which the balloon is inflated to effect the dilatation of the stenosis. In this embodiment liquid is applied to inflation port 60. Inflation port 58 may be exposed to atmospheric pressure or, if desired, to reduced pressure. The catheter may be maintained in this configuration for as long as desired by the physician to effect the angioplasty. At the completion of dilatation of the stenosis the balloon is deflated by aspiration through port 60 thereby enabling withdrawal of the catheter from the artery.

From the foregoing it will be appreciated that the invention provides a catheter having a plurality of lumens in which the overall cross-sectional area defined by the catheter may be maintained relatively low while selectively maintaining the cross-sectional area of the individual lumens at a maximum. When used in a balloon dilatation catheter the invention enables manipulation of the configuration of the catheter such that in the separate operating modes of the catheter, the operating lumen may be maintained at a maximum cross-sectional area. Additionally, in a modified form of angioplasty catheter in accordance with the invention the catheter incorporates an arrangement by which the catheter may be coupled to the guidewire so that the guidewire may provide added column support for the catheter and enhance the pushability of a catheter, particularly through a tight stenosis.

It should be understood, however, that the foregoing description of the invention is intended merely to be illustrative thereof and that other modifications and embodiments may be apparent to those skilled in the art without departing from its spirit. For example, although the invention is particularly useful with a balloon dilatation catheter, its principles may be used in other types of multilumen catheters.

Having thus described the invention, what I desire to claim and secure by letters patent is:

1. A balloon dilatation catheter comprising:
   a longitudinally flexible tubular shaft having a proximal end and a distal end and a passageway with a cross sectional area, said passageway extending through the shaft from the shaft proximal end to the shaft distal end, the shaft being constructed and arranged to be relatively radially inflexible whereby the shaft will have substantially constant inner and outer cross sectional dimensions;
   a thin walled, flexible, collapsible inner tube having an inner lumen therethrough, said inner tube being radially and longitudinally flexible and extending through the passageway, and being attached to the shaft at fixed locations at each of the proximal and distal ends so as to form an annular inflation lumen between the shaft and the inner tube, the inner lumen defining a guide wire lumen extending from the shaft proximal end to the shaft distal end;
   a dilatation balloon mounted on the shaft at the shaft distal end and in fluid communication with the inflation lumen; and
   means for introducing pressurized fluid into the inflation lumen in order to expand the dilatation balloon, the inner tube being sufficiently flexible so that fluid pressure against the inner tube walls collapses the guide wire lumen along its entire length and causes the inflation lumen to expand along its entire length, said shaft being sufficiently radially inflexible that said cross sectional area of said passageway and the cross sectional dimensions of the shaft remain substantially constant when said pressurized fluid is introduced into said inflation lumen.

2. A balloon dilatation catheter as defined in claim 1 further comprising, in combination, a guidewire extending through the guidewire lumen.

3. A balloon dilatation catheter as defined in claim 1 further comprising an inlet means for providing fluid communication between the inflation lumen and a source of fluid pressure.

4. A balloon dilatation catheter as defined in claim 3 wherein the inlet means comprises an inlet port extending through the wall of the outer tube.

5. A balloon dilatation catheter as defined in claim 3 wherein the cross-sectional areas of the inflation lumen and the guidewire lumen are dependent on the pressure applied to the inflation lumen.

6. A balloon dilatation catheter as defined in claim 1 wherein the flexible inner tube is formed from a polymeric material.

7. A balloon dilatation catheter as defined in claim 6 wherein the polymeric material is polyethylene terephthalate.

8. A balloon dilatation catheter as defined in claim 1 wherein the inner tube has a wall thickness of approximately 0.001 inches.

9. A balloon dilatation catheter as defined in claim 1 wherein the shaft is formed from a polymeric material.

10. A balloon dilatation catheter as defined in claim 9 wherein the polymeric material is polyethylene.

11. A balloon dilatation catheter as defined in claim 1 wherein the dilatation balloon is formed from a polymeric material.

12. A balloon dilatation catheter as defined in claim 11 wherein the polymeric material is polyethylene terephthalate.

13. A balloon dilatation catheter as defined in claim 1 further comprising a tubular member surrounding a portion of the tubular shaft.

14. A balloon dilatation catheter as defined in claim 13 wherein the tubular member is formed from stainless steel.

15. A balloon dilatation catheter comprising:
   a elongated flexible tubular shaft having a proximal end and a distal end and a passageway with a cross sectional area, said passageway extending longitudinally through the shaft;
   a plurality of thin walled flexible inner members attached to the shaft distal end and dividing the lumen of the shaft into a plurality of lumens including at least a guidewire lumen open at both ends of the catheter, an inflation lumen and an intermediate lumen between the inflation and guidewire lumens, said intermediate lumen being sealed at the shaft distal end;
   a balloon mounted on the distal end of the catheter and being in communication with the inflation lumen, the other end of the inflation lumen being in communication with a source of liquid under pressure;
   a port communicating with the intermediate lumen for selectively pressurizing or depressurizing the intermediate lumen, the inner members being sufficiently flexible so that the inflation lumen and the guidewire lumen collapse when the intermediate lumen is pressurized; and
   a port communicating with the inflation lumen for selectively pressurizing or depressurizing the inflation lumen, the inner members being sufficiently flexible so that the guidewire lumen and the intermediate lumen collapse when the inflation lumen is pressurized, said shaft being sufficiently inflexible that said cross sectional area of said passageway remains substantially constant when said inflation lumen and said intermediate lumen are pressurized.

16. A balloon dilatation catheter comprising:
   a elongated flexible tubular shaft having a proximal end and a distal end and a passageway extending therethrough;
   a plurality of thin walled flexible inner members attached to the shaft distal end and dividing the lumen of the shaft into a plurality of lumens including at least a guidewire lumen open at both ends of the catheter, an inflation lumen and an intermediate lumen between the inflation and guidewire lumens;
   a balloon mounted on the distal end of the catheter and being in communication with the inflation lumen, the other end of the inflation lumen being in communication with a source of liquid under pressure;
   a port communicating with the intermediate lumen for selectively pressurizing or depressurizing the intermediate lumen, the inner members being sufficiently flexible so that the inflation lumen and the guidewire lumen collapse when the intermediate lumen is pressurized; and
   a port communicating with the inflation lumen for selectively pressurizing or depressurizing the inflation lumen, the inner members being sufficiently flexible so that the guidewire lumen and the intermediate lumen collapse when the inflation lumen is pressurized; wherein said flexible members comprise generally concentric, thin wall flexible tubes each having a proximal end and a distal end, the distal ends of the tubes being sealed to each other in order to seal the distal end of the intermediate lumen and the end of the tubes being sealed to the distal end of the tubular catheter shaft in order to seal the distal end of the inflation lumen.

17. A balloon dilatation catheter as defined in claim 16 wherein said flexible tubular members comprise:
an inner tubular member defining a guidewire lumen;
an outer tubular member defining an inflation lumen in cooperation with the inner surface of the tubular catheter shaft and an intermediate lumen in cooperation with the inner flexible tube.

18. A method of performing a medical procedure which involves inflation and deflation of a balloon within a patient body, said method comprising:
providing a balloon dilatation catheter having a tubular shaft with a proximal end and a distal end and a passageway extending therethrough, a balloon mounted in a fixed location on the exterior of the shaft on said distal end, the passageway being divided into at least first and second lumens by a flexible dividing element connected to said distal catheter end and extending along substantially the entire length of the passageway, the first lumen being in fluid communication with the balloon;
inserting the balloon dilatation catheter into the patient body;
expanding the second lumen by aspirating the balloon via the first lumen by removing fluid from the first lumen, pressure in the second lumen pressing against the flexible dividing element and causing the first lumen to collapse along the entire length of the catheter portion while the balloon is collapsed about the exterior of the shaft; and
inflating the balloon by pressurizing the balloon via the first lumen by applying pressurized fluid to the first lumen, the pressurized fluid in the first lumen pressing against the flexible dividing element and causing the second lumen to collapse along the entire length of the catheter portion.

19. A method for performing a medical procedure as defined in claim 18 wherein the first lumen is adapted to transmit an inflation fluid.

20. A method for performing a medical procedure as defined in claim 18 wherein the second lumen is adapted to receive a guidewire.

21. A method for performing an angioplasty procedure comprising:
providing a catheter having a flexible tubular shaft with a proximal end and a distal end and at least one inner flexible divider dividing the interior of the tubular shaft into a plurality of lumens including a guidewire lumen and an inflation lumen, the guidewire lumen being open at its opposite ends and the inflation lumen being open at the catheter shaft proximal end and sealed at the catheter shaft distal end and in communication with the interior of a balloon mounted at the distal end of the catheter shaft;
advancing the catheter having a guidewire in the guidewire lumen through the patient's arteries toward the site of a stenosis to be dilated;
aspirating the balloon inflation lumen to cause the flexible divider to flex and reduce the cross-sectional area of the balloon inflation lumen along its entire length and simultaneously expand the cross-sectional area of the guidewire lumen along its entire length;
then advancing the catheter over the guidewire while maintaining the balloon in a deflated configuration and pushing the balloon into the stenosis;
while the balloon is disposed within the stenosis applying fluid under pressure to the inflation lumen to inflate the balloon and effect the dilatation of the stenosis, said flexible member contracting about the guidewire along its entire length during said inflation thereby to maximize the cross-sectional flow area of the inflation lumen; and thereafter deflating the lumen by applying a negative pressure to the inflation lumen.

22. A method as defined in claim 21 further comprising:
providing an additional flexible divider element within the catheter to define an intermediate lumen between the inflation and guidewire lumens;
during the step of advancing the catheter into the stenosis, maintaining the intermediate lumen in a pressurized condition to cause the cross-sectional area of the intermediate lumen to expand and the cross-sectional area of the guidewire lumen to contract to securely couple the catheter to the guidewire and, while so-coupled, advancing the catheter together with the guidewire through the stenosis.

* * * * *